(12) United States Patent
Bleuler et al.

(10) Patent No.: US 10,094,772 B2
(45) Date of Patent: Oct. 9, 2018

(54) DEVICE FOR THE CONTACTLESS AND NON-DESTRUCTIVE TESTING OF A SURFACE BY MEASURING ITS INFRARED RADIATION

(71) Applicant: CoatChecker GmbH, Winterthur (CH)

(72) Inventors: Alexander Bleuler, Neerach (CH); Joris Storskogen, Zurich (CH); Nusret Salihi, Zurich (CH); Nils Reinke, Winterthur (CH)

(73) Assignee: CoatChecker GmbH, Winterthur (CH)

( * ) Notice: Subject to any disclaimer, the term of this patent is extended or adjusted under 35 U.S.C. 154(b) by 0 days.

(21) Appl. No.: 15/618,841

(22) Filed: Jun. 9, 2017

(65) Prior Publication Data
US 2017/0356844 A1 Dec. 14, 2017

(30) Foreign Application Priority Data
Jun. 10, 2016 (EP) ..................................... 16001320

(51) Int. Cl.
| G01J 3/00 | (2006.01) |
| G01N 21/3563 | (2014.01) |
| G01N 1/42 | (2006.01) |
| G01N 21/55 | (2014.01) |
| H05K 7/20 | (2006.01) |
| G01N 25/72 | (2006.01) |

(52) U.S. Cl.
CPC ........... *G01N 21/3563* (2013.01); *G01N 1/42* (2013.01); *G01N 21/55* (2013.01); *G01N 25/72* (2013.01); *H05K 7/20136* (2013.01)

(58) Field of Classification Search
CPC .. G01N 21/314; G01N 21/33; G01N 21/3504; G01J 3/10; G01J 3/42

USPC .......................................................... 356/51
See application file for complete search history.

(56) References Cited

U.S. PATENT DOCUMENTS

| 4,708,482 A | 11/1987 | Neiheisel |
| 6,375,908 B1* | 4/2002 | Kaszas-Savos ........ B01D 53/64 110/216 |
| 2001/0001391 A1* | 5/2001 | Kamieniecki ..... H01L 21/02046 134/1 |
| 2005/0274661 A1* | 12/2005 | Jackson ............... B01D 5/0072 55/385.1 |

(Continued)

FOREIGN PATENT DOCUMENTS

DE 102012103975 B3 8/2013

*Primary Examiner* — Md M Rahman
(74) *Attorney, Agent, or Firm* — The Webb Law Firm

(57) ABSTRACT

A device (100) for the contactless non-destructive testing of a surface (106) by measuring its infrared radiation includes an electromagnetic radiation source (1) emitting excitation radiation which is directed onto the surface (106) to be tested (26), a detector (9) arranged in a direction towards said surface (106) and a first IR filter medium (2) provided between the radiation source (1) and the surface (106). In response to radiation impinging onto the surface (106), detection radiation is emitted by the surface (106) and fed to the detector (9). At least a second filter medium (3) is provided between the first filter medium (2) and the surface (106) to be tested (26), wherein a space (24) is provided between the first and the second filter medium (2, 3) creating a coolant channel and being connected to a coolant drive for actively exchanging the fluid for the cooling fluid circulation (4).

12 Claims, 4 Drawing Sheets

(56) References Cited

U.S. PATENT DOCUMENTS

| | | | |
|---|---|---|---|
| 2006/0096677 A1 | 5/2006 | Camm et al. | |
| 2006/0283790 A1* | 12/2006 | Elkins | G21C 3/3206 |
| | | | 210/335 |
| 2008/0117401 A1* | 5/2008 | Tani | G03F 7/70341 |
| | | | 355/67 |
| 2011/0146318 A1* | 6/2011 | Wittmann | B60H 1/00514 |
| | | | 62/238.7 |
| 2012/0267546 A1* | 10/2012 | Reynolds | B01D 8/00 |
| | | | 250/423 R |
| 2013/0037720 A1 | 2/2013 | Reinke et al. | |
| 2014/0252232 A1* | 9/2014 | Reinke | G01N 21/55 |
| | | | 250/338.1 |
| 2015/0322893 A1* | 11/2015 | Milton | F02M 21/0221 |
| | | | 55/385.3 |

* cited by examiner

DEVICE FOR THE CONTACTLESS AND NON-DESTRUCTIVE TESTING OF A SURFACE BY MEASURING ITS INFRARED RADIATION

CROSS-REFERENCE TO RELATED APPLICATION

This application claims priority to European Patent Application No. 16 001 320.7 filed Jun. 10, 2016, the disclosure of which is hereby incorporated in its entirety by reference.

BACKGROUND OF THE INVENTION

Field of the Invention

The present invention relates to a device for the contactless and non-destructive testing of a surface by measuring its infrared radiation.

Description of Related Art

The contactless testing of surfaces based on the generation and measurement of transient periodic heating and cooling processes uses an excitation source for heating the surface to be tested as well as an infrared detector which measures the infrared radiation from the heated surface. This method is called photothermy if electromagnetic radiation in the ultraviolet, optical or infrared range is used for excitation.

Such a device is described in US 2013/0037720 using one or more incoherent electromagnetic radiation sources, a detector providing and arrange on an detection axis and comprising a measuring area a testing area defining an area to be measured of the test surface and an imaging device arranged on the detection axis for mapping the testing area onto the measuring area of the detector. The radiation sources are adapted to generate a pulse like or intensity modulated excitation radiation, e.g. flash lights directed onto the surface to be tested in the testing area. The device according to US 2013/0037720 uses e.g. flash lamps allowing to provide a measurement to evaluate the exact thickness of a surface coating having a value between several micrometers and up to 0.1 millimeter.

SUMMARY OF THE INVENTION

The prior art device is adapted to evaluate at least one of the group of physical properties from thickness, thermal diffusivity, thermal effusivity, thermal conductivity, heat capacity, density, adhesion, porosity, composition, degree of hardening or phase of one or more thin coatings applied to a substrate. The substrate can be a sheet of metal and the coatings have a thickness of e.g. 10 to 100 micrometer. The prior art device is not capable to determine such properties, if the underlying substrate is a thick body as a cement brick. It is also not capable to evaluate such properties, if the thickness of the coating is 1 millimeter to 10 millimeter. Such a device cannot be used to provide a thickness indication for test specimen having a body with a thickness of several centimeters.

It is a further object of the present invention to provide the measuring device as a handheld mobile device since the coatings to be tested are often in e.g. building structures and cannot be transferred into a laboratory environment.

The object of the invention is achieved with a device for the contactless and non-destructive testing of a surface by measuring its infrared radiation thereof, comprising: one or more electromagnetic radiation sources adapted to emit excitation radiation which can be directed onto the surface to be tested; a detector arranged on a detection axis directed towards the surface to be tested; and a first IR filter medium provided between each radiation source and the surface to be tested, wherein, in response to radiation impinging onto the surface to be tested, detection radiation is emitted by the surface to be tested and fed to the detector, wherein at least a second filter medium is provided between the first filter medium and the surface to be tested, wherein a space is provided between the first and the second filter medium creating a coolant channel for a cooling fluid circulation and wherein the coolant channel is connected to a coolant drive for actively exchanging the fluid for the cooling fluid circulation.

Preferably, two insulation walls are provided between each electromagnetic radiation source and the detector, wherein a space is provided between the first and the second insulation wall creating a coolant channel for a cooling fluid circulation.

The coolant channel for the filter media and the coolant channel of the insulation walls are directly connected; then a continuous cooling channel can be provided where a cooling gas is blown through the channel. It is a further advantage, if the coolant flow is initially directed between the filter media, or glass sheets for the transmittal of the excitation radiation, and then to direct the preheated fluid between the insulation walls.

The device preferably comprises housing walls having free ends adapted to be applied against the surface to be tested, creating a free space between the surface to be tested and the second filter medium creating a further coolant channel for a cooling fluid circulation.

The fluid can be an inert gas, especially nitrogen. Then the coolant drive can be a blower. The fluid can also be a liquid, if the coolant channels are hermetically sealed. The coolant drive would then be a pump.

An imaging device can be arranged on the detection axis for mapping the surface to be tested onto the detector.

The excitation radiation from the radiation sources can be fed to the surface to be tested at an inclination to the detection axis avoiding direct reflection of remaining IR excitation portions. An imaging device can be arranged between the radiation source and the surface to be tested.

A control unit is used to determine, based on the measured IR response from the detector, at least one of the group of physical properties from thickness, thermal diffusivity, thermal effusivity, thermal conductivity, heat capacity, density, adhesion, porosity, composition, degree of hardening or phase of one or more coatings applied to a substrate.

The electromagnetic radiation sources may be incoherent electromagnetic radiation sources.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
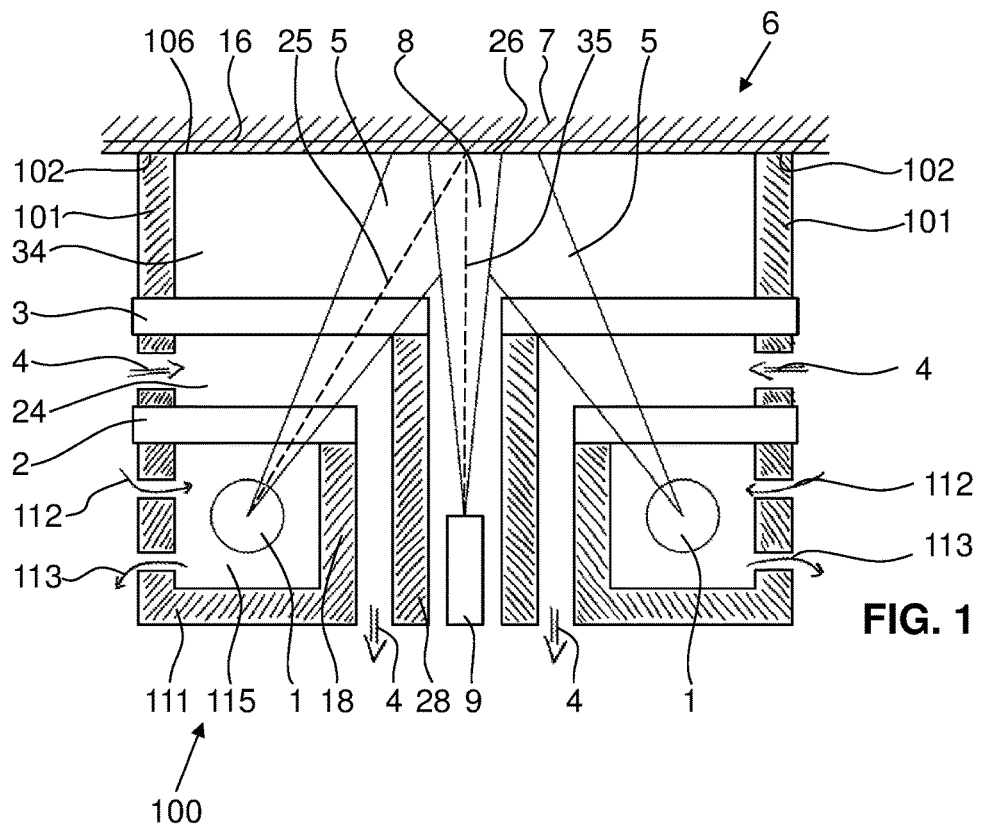
FIG. 1 shows a schematic cross section view of a device according to a first embodiment of the invention applied against a surface to be tested.

FIG. 1 shows a schematic cross-section view according to an embodiment of the invention wherein the device is a handheld device 100 applied against a surface to be tested being part of the test specimen 6. It is noted that the device 100 has side walls 101 with a free end surface 102 to be positioned against the surface 106 of the material to be tested. The body of the testing device 100 with said side walls 101 has back walls 111 forming a handheld device, which can have attachments, handles, power lines or it can be a battery operated testing device 100.

Reference numeral 1 relates to radiation sources especially capable to provide radiation outside the IR-range. The cross-section view of FIG. 1 can relate to two sources 1 directing their excitation radiation 5 according to the main optical axis 25 of the radiation source towards the testing surface 26 on test specimen 6 from which radiated heat radiation 8 is emitted and targets an infrared detector 9 provided somewhere in between the radiation sources 1 as shown in FIG. 1. A collimating element can be provided along the optical axis 35 of the detector 9. It is of course possible that the radiation sources 1 are arranged in a circle around the testing surface 26 with a central detector. In any case, it is preferred that at least one insulation wall 18 and/or 28 is provided between the radiation source 1 and the detector 9.

The radiation leaving the radiation source 1 in the beam 5 passes through at least two filter media 2 and 3 separated by a free space 24. Between the filter surface 3, which is nearer to the surface layer 16 to be tested, and said surface layer 16 is a further free space 34.

In the embodiment shown in FIG. 1, the free space 24 in front of the radiation source 1, i.e. between the radiation source 1 and the surface to be tested 106 provides a channel for a coolant medium which flows according to arrow 4 through the side wall 101 and leaves the device at the back wall 111. Therefore, it flows between the insulation walls 18 and 28 in parallel to the side walls 101 and vertically to the surface 106 to be tested. This coolant flow, which is provided for both radiation sources, avoids a significant rise in temperature and heating of the filter media 2 and 3 (to a predetermined extent) as well as of the insulation walls 18 and 28. Thus, it will be mainly the radiation from the radiation sources 1 which heats up the body base element 7 at its surface 106 as well as it avoids a direct heating of the detector 9 through infrared radiation coming from said intermediate walls 18 and 28 and/or from said optical wall elements. It is of course possible to invert the flow direction 4 to the opposite direction of the arrows 4, especially in view of the fact that a greater heat impact will probably be provided by the filter media 2 and 3 in comparison to the IR radiation coming from the insulation walls 18 and 28. Filter media 2 and 3 can be made of glass or acryl glass.

In the embodiment of FIG. 1, it may also be provided an optional inlet and outlet in relation to the free space 34 but this is not shown in the drawing. Additionally, the side walls 101 have an inlet 112 and an outlet 113 for each radiation source 1 to allow a further coolant flow through the radiation source cavity 115.

The coolant medium is preferably just air or a gas and specifically an inert gas as nitrogen. Using a fluid medium for the coolant channel 24 is in principle possible since the radiation has just to pass the filter medium 2 and 3 which is in principle possible without any contact with the lamp arrangements.

The radiation sources 1 are acting for longer times between 0, 1 and 1000 seconds depending on the materials and thickness in order to deposit a high amount of energy in the testing area 26 to heat the surface layer 16 having a thickness of up to several millimeters. Exposition times between 1 and 100 seconds are preferred. This high input of energy as well as the longer use of the radiation sources 1 creates secondary infrared centers which have to be avoided through taking away the heated up materials through the coolant flow. The coolant channels 24 are not only provided in the drawing plane but preferably encompass the radiation sources 1 on all side where radiation can be emitted and be directed into the direction of the sensor 9.

The coolant flow according to the coolant flow direction 4 and between inlet 112 and outlet 113 can be closed into a coolant cycle or coolant circuit with a coolant drive (not shown), effectively exchanging the coolant or cooling fluid being in the spaces 24 and 115.

The coolant or cooling fluid can be a gas and then the coolant drive can be a blower. The coolant or cooling fluid can be a liquid and then the coolant drive can be a pump.

Figure 2:
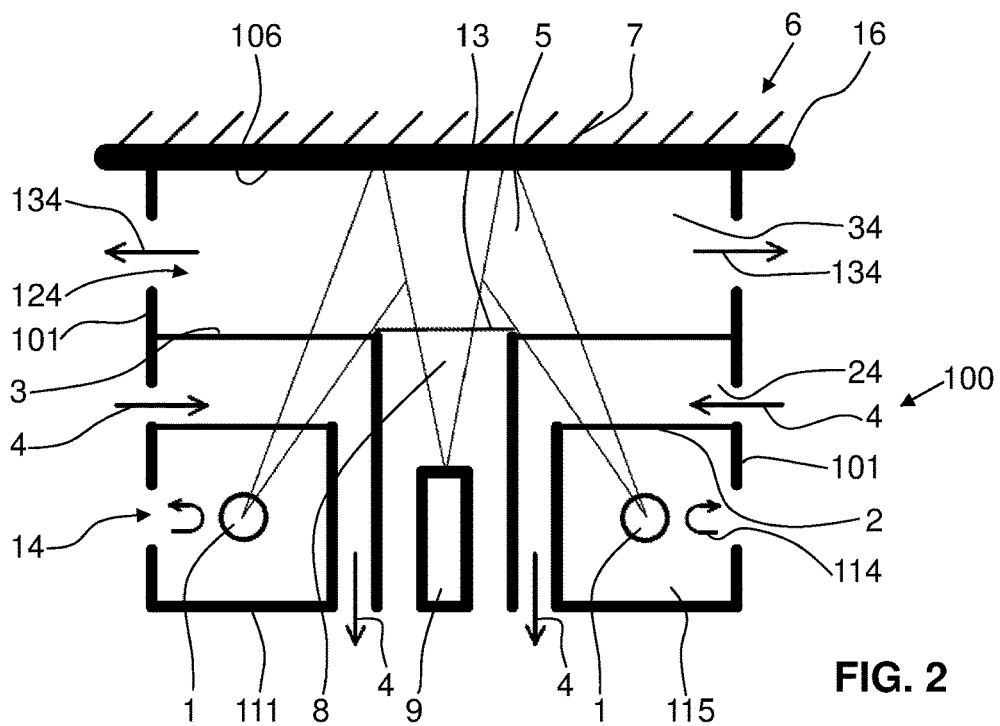
FIG. 2 shows a schematic cross section view of a device according to a second embodiment of the invention applied against a surface to be tested.

FIG. 2 shows a schematic cross-section view according to a second embodiment of the invention wherein the device is also a handheld device 100. Same reference numerals throughout the drawings are related to identical features in different embodiments.

The test specimen 6 has a surface layer 16 of a thickness which is to be determined. An usual thickness for this testing device is between Device 100 with side walls 101 and back walls 111 is applied onto the surface layer 16 creating the free space 34 shielded from the excitation source 1 through optical windows and filter media 2 and 3 and thus behind the coolant channel 24. Here the radiation sources 1 are provided inside source cavity 115 having an opening 14 for the inlet and outlet of coolant medium according to circular flow 114. In difference to the embodiment of FIG. 1 the free space 34 has through side openings 124 connections to the environment where a test specimen near coolant flow 134 takes away any heat from the inside surface of filter medium 3 and central filter medium 13. Central filter medium 13 can be a lens collimating radiation from the testing surface 26 and is a pass filter for IR radiation. Nevertheless lens 13 provides a clear physical separation between the free space 34 on the side near the surface layer 16 to be tested and the sensor 9 so that no medium flow is possible between the free space 34 and the area around sensor 9.

The coolant flow according to the coolant flow direction 4 and outlet flow 134 can be enhanced through blowers (not shown), effectively exchanging the fluid being circulated in the spaces 24, 34 and 115, thus reducing the impact of heated walls 18 and 28 as well as optical filter media 2 and 3.

Figure 3:
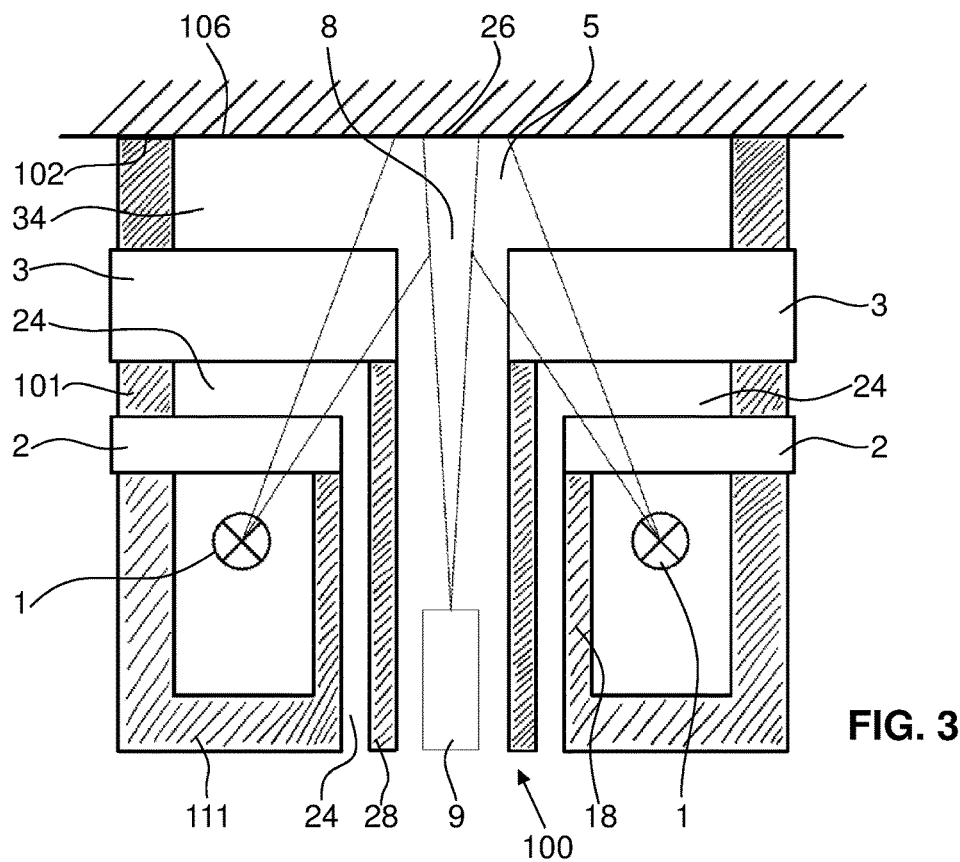
FIG. 3 shows a schematic cross section view of a device according to a third embodiment of the invention applied against a surface to be tested.

FIG. 3 shows a schematic cross-section view according to a third embodiment of the invention wherein the device is also a handheld device 100. The main difference between the embodiments of FIG. 1 and FIG. 2 and the embodiment of FIG. 3 is the absence of dedicated coolant channels. Space 24 is only connected to the back room, the same is true for the front space 34, which is only connected via the central radiation channel with the environment. Filter medium 3 nearer to the testing surface 26 is far thicker than the filter medium 2 on the other side of the free space 24. This thicker filter medium 3 provides the advantage of better insulation of the remaining direct heating radiation onto the testing area.

Figure 4:
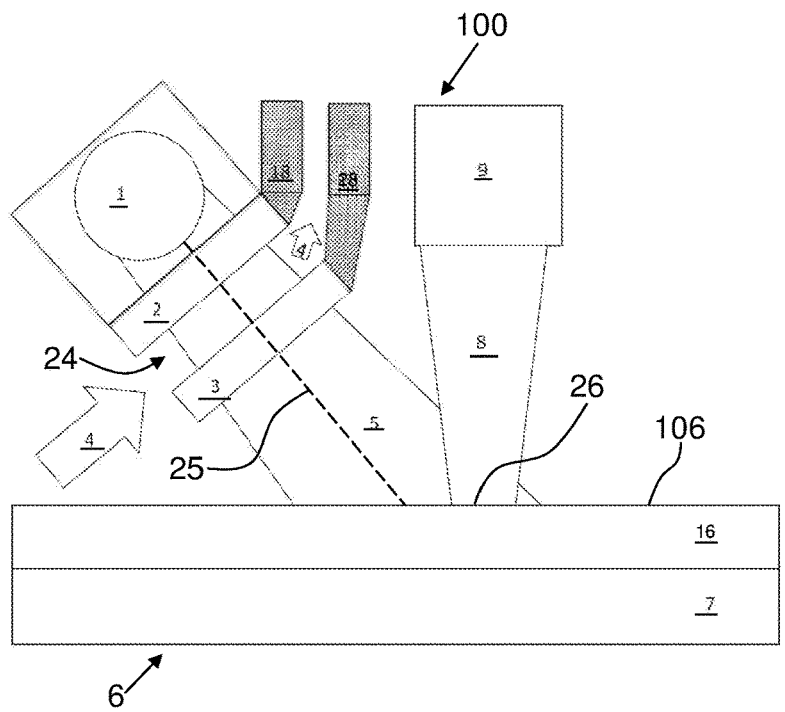
FIG. 4 shows a very schematic cross section view of a device according to a fourth embodiment of the invention.

FIG. 4 shows a very schematic cross section view of a device according to a fourth embodiment of the invention. The device 100 according to FIG. 4 can have distance enabling elements to apply the device against a surface 106 to be tested. Therefore side walls 101 with a free end surface 102 to be positioned against the surface 106 of the material to be tested are not shown.

Reference numeral 1 relates to one radiation source capable to provide radiation outside the IR-range. The cross-section view of FIG. 4 can also relate to more sources 1 outside the drawing plane and directing their excitation radiation 5 towards the testing surface 26 of test specimen 6 from which radiated heat radiation 8 is emitted and targets an infrared detector 9 provided somewhere in between the radiation sources 1 as shown in FIG. 1. The surface to be tested comprise a layer or coating 16 and a base element 7. The base element 7, e.g. a ciment brick, having a thickness of several centimeters is covered by a surface layer 16 of one to several millimetres and it is one aim of the invention to correctly evaluate the thickness of layer 16. Possible materials to be tested are rubber, plastics, ceramic materials, wood, metal, leather, paint, glass and ciment. The filter media 2 and 3 are provided in an oblique manner with their main optical axis 25 directed towards the testing area 26. In any case, it is preferred that at least one insulation wall 18 and/or 28 is provided between the radiation source 1 and the detector 9 with a coolant flow 4 in between. The walls 18 and 28 are shielding the detector 9 from a direct IR exposure from the radiation source(s) 1. The two filter media 2 and 3 with its intermediate coolant flow 4 are shielding the detector 9 from a reflected or diffracted IR exposure from the radiation source(s) 1.

A reflector element (not shown) can be provided behind and around the excitation source 1 in the cavity 115.

One or the other filter medium 2 or 3 can also be a lens to focus the excitation beam 5 on the testing area 26 including a spectral filtering. It is also possible to provide a third filter medium in front of said two filter media 2 and 3 creating a further second parallel free space 24 to shield the testing surface 26 even more efficiently from a direct IR heating.

Figure 5:
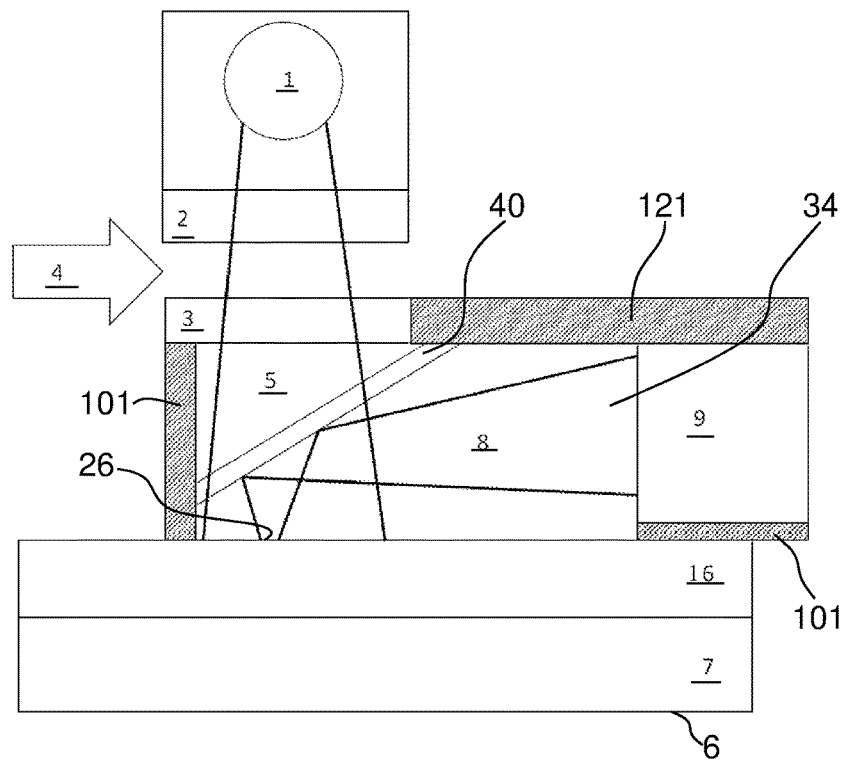
FIG. 5 shows a very schematic cross section view of a device according to a further embodiment of the invention.

FIG. 5 shows a very schematic cross section view of a device according to a further embodiment of the invention. The device 100 according to FIG. 5 comprises a reflective/transmissive element 40. It is transmissive for the excitation radiation emitted from the radiation source 1 and it is reflective for IR radiation emitted from the surface 26 of specimen 6 to be tested. The reflective/transmissive element 40 is positioned in a predetermined angle to reflect the heat radiation 8 onto the detector provided on the side.

Here, elements 101 and 121 of a housing are shown. There will be further elements encompassing the lamp and radiation source 1 with the IR filter medium 2 and the side wall 101 as well as the detector cavity back wall 121 which will be readily added by persons skilled in the art. Detector 9 closes the right side with side wall 101 and back wall 121 creating the separated further space 34 as already shown in FIG. 1.

Figure 6:
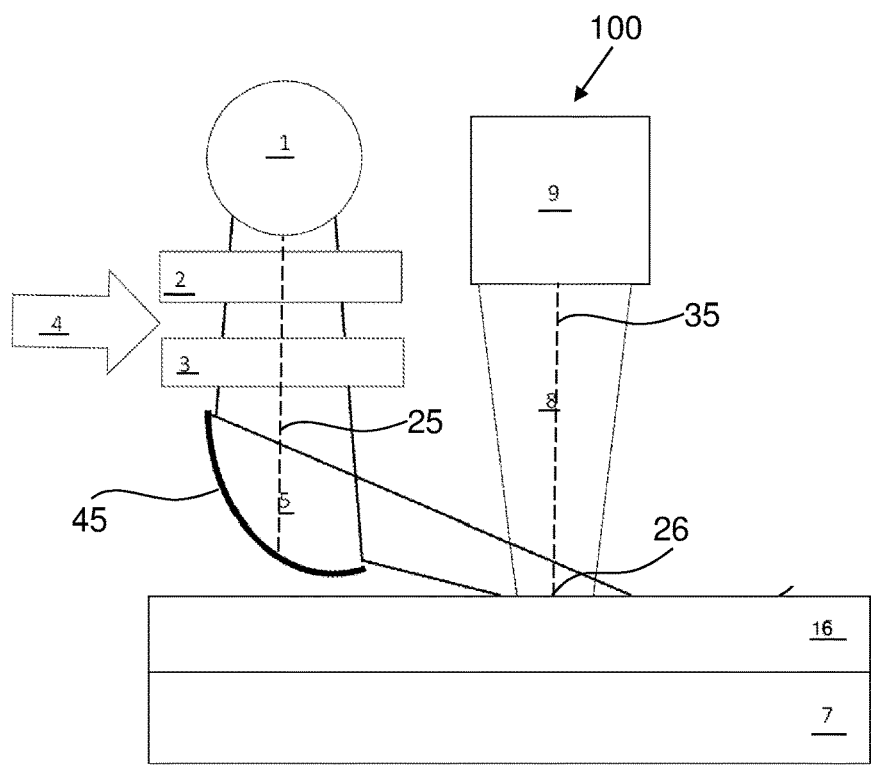
FIG. 6 shows a very schematic cross section view of a device according to a further embodiment of the invention.

FIG. 6 shows a very schematic cross section view of a device according to a further embodiment of the invention. The device 100 according to FIG. 6 comprises a reflective collimating mirror 45. Radiation source 1 and detector 9 are mounted with parallel main optical axes 25 and 35. Then the excitation beam 5 directed towards the reflective collimating mirror 45 is diverted towards the testing area 26. Therefore any IR portion of the excitation radiation 1 will be mainly reflected in a very different direction than the IR radiation detected by detector 9 along its optical axis 35.

As explained with FIGS. 5 and 6, the differentiating features of one of the embodiments from FIGS. 1 to 4 can be combined with further features from any other embodiment.

So it is possible to add shielding walls 18 and 28 to the embodiments of FIG. 5 or 6 and imaging elements like the central filter medium 13 can be added as well.

Figure 7:
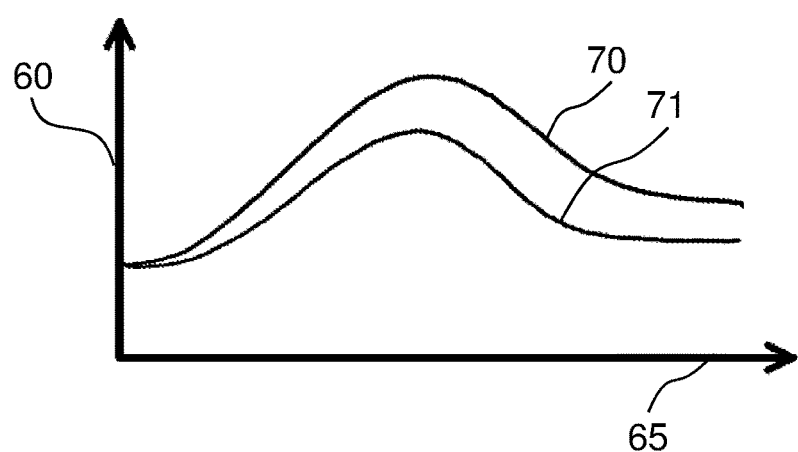
FIG. 7 shows a diagram of temperature against time.

FIG. 7 shows a diagram of temperature against time. A control unit is integrated in device 100 or attached to device 100 to handle the sensor output of detector 9. It provides the curve 70 of the temperature in Kelvin as result of the received radiation and the time passed receiving the radiation which may have already stopped for a coating of a specific thickness on a substrate. A further coating having a different thickness on the same substrate provides the curve 71. Then the control unit is adapted to calculate a thickness value for the coating.

| LIST OF REFERENCE SIGNS | |
|---|---|
| 1 | radiation source |
| 2 | filter medium |
| 3 | filter medium |
| 4 | coolant flow direction |
| 5 | excitation radiation |
| 6 | test specimen |
| 7 | base element |
| 8 | heat radiation |
| 13 | central filter medium |
| 14 | opening |
| 16 | surface layer |
| 18 | insulation wall |
| 24 | coolant channel |
| 25 | main optical axis of radiation source |
| 26 | testing surface |
| 28 | insulation wall |
| 34 | further free space |
| 35 | optical axis of detector |
| 40 | reflective/transmissive element |
| 45 | collimating mirror |
| 60 | temperature |
| 65 | time |
| 70 | detector curve of a coating |
| 71 | detector curve of a different coating |
| 100 | testing device according to a first embodiment |
| 101 | side wall |
| 102 | free end surface |
| 106 | surface |
| 111 | back wall |
| 112 | inlet |
| 113 | outlet |
| 114 | circular flow |
| 115 | source cavity |
| 121 | detector cavity back wall |
| 124 | side opening |
| 134 | test specimen near coolant flow |

The invention claimed is:

1. A device for the contactless and non-destructive testing of a surface by measuring its infrared radiation thereof, comprising:
   one or more electromagnetic radiation sources adapted to emit excitation radiation which can be directed onto a surface to be tested;
   a detector arranged on a detection axis directed towards the surface to be tested;
   a first IR filter medium provided between each radiation source and the surface to be tested;
   at least a second filter medium provided between the first IR filter medium and the surface to be tested; and
   a first coolant channel for a cooling fluid circulation created as a space between the first and the second filter medium,
   wherein, in response to excitation radiation impinging onto the surface to be tested, detection radiation is emitted by the surface to be tested and fed to the detector, wherein the coolant channel is connected to a coolant drive for actively exchanging the fluid for the cooling fluid circulation, wherein a first insulation wall and a second insulation wall are provided between the one or more electromagnetic radiation sources and the detector, wherein a space is provided between the first insulation wall and the second insulation wall creating a second coolant channel for a cooling fluid circulation.

2. The device according to claim 1, wherein the first coolant channel for the first and the second filter medium and the second coolant channel of the first and the second insulation walls are directly connected.

3. The device according to claim 1, wherein the coolant drive and connected cooling channel(s) are forming a closed circuit.

4. The device according to claim 1, wherein the cooling fluid is a gas and the coolant drive is a blower.

5. The device according to claim 1, wherein the cooling fluid is a liquid and the coolant drive is a pump.

6. The device according to claim 1, further comprising housing walls having free ends adapted to be applied against the surface to be tested, creating a free space between the surface to be tested and the second filter medium creating a further coolant channel for a cooling fluid circulation.

7. The device according to claim 1, wherein the fluid is an inert gas.

8. The device according to claim 7, wherein the fluid is nitrogen.

9. The device according to claim 1, wherein an imaging device is arranged on the detection axis for mapping the surface to be tested onto the detector.

10. The device according to claim 1, wherein the excitation radiation from the radiation sources is fed to the surface to be tested at an inclination to the detection axis.

11. The device according to claim 1, wherein an imaging device is arranged between the radiation source and the surface to be tested.

12. The device according to claim 1, further comprising a control unit to determine, based on a measured IR response from the detector, at least one of the group of physical properties of one or more coatings applied to a substrate consisting of: thickness, thermal diffusivity, thermal effusivity, thermal conductivity, heat capacity, density, adhesion, porosity, composition, degree of hardening, and phase.

* * * * *